(12) United States Patent
Lee

(10) Patent No.: US 7,207,338 B2
(45) Date of Patent: Apr. 24, 2007

(54) TOOTH-CLEANING PAPER COMBINED WITH DENTAL FLOSS

(76) Inventor: Jong-Soo Lee, 25-206 Banpo-jugong Apt., 1020 Banpo-bondong, Seocho-gu, Seoul137-811 (KR)

( * ) Notice: Subject to any disclaimer, the term of this patent is extended or adjusted under 35 U.S.C. 154(b) by 21 days.

(21) Appl. No.: 10/493,174

(22) PCT Filed: Nov. 11, 2002

(86) PCT No.: PCT/KR02/02098

§ 371 (c)(1),
(2), (4) Date: Oct. 14, 2004

(87) PCT Pub. No.: WO03/041608

PCT Pub. Date: May 22, 2003

(65) Prior Publication Data

US 2005/0034741 A1 Feb. 17, 2005

(30) Foreign Application Priority Data

Nov. 15, 2001 (KR) ............... 20-2001-0035163

(51) Int. Cl.
*A61C 15/00* (2006.01)
(52) U.S. Cl. ............... 132/323; 132/321
(58) Field of Classification Search ........ 132/321–324, 132/329; 206/63.5, 368, 581, 428; 15/104.93
See application file for complete search history.

(56) References Cited

U.S. PATENT DOCUMENTS

| | | | |
|---|---|---|---|
| 2,828,754 A * | 4/1958 | Stewart ............ 132/323 |
| 3,754,332 A * | 8/1973 | Warren, Jr. ............ 433/217.1 |
| 4,998,978 A * | 3/1991 | Varum ............ 132/321 |
| 5,014,725 A * | 5/1991 | Patscot et al. ............ 132/324 |
| 5,524,764 A | 6/1996 | Kaufman et al. ............ 206/581 |
| 5,771,522 A | 6/1998 | Carmody ............ 15/208 |
| 5,787,907 A * | 8/1998 | Endelson ............ 132/321 |
| 5,819,765 A | 10/1998 | Mittiga ............ 132/309 |
| 6,378,698 B1 * | 4/2002 | Scoggins ............ 206/205 |
| 6,464,103 B1 * | 10/2002 | Schroeder ............ 221/47 |

FOREIGN PATENT DOCUMENTS

JP 7-24313 5/1995

OTHER PUBLICATIONS

PCT International Search Report; International Application No. PCT/KR02/02098; International Filing Date: Nov. 11, 2002; Date of Mailing: Mar. 21, 2003.

* cited by examiner

*Primary Examiner*—Cris L. Rodriguez
*Assistant Examiner*—Rachel A. Running
(74) *Attorney, Agent, or Firm*—Cantor Colburn LLP

(57) ABSTRACT

Disclosed is a tooth-cleaning paper combined with dental floss, in which the tooth-cleaning paper is formed of a thin paper or a gauze sterilized and wetted with an aqueous fluoride solution and has a plurality of edge cuts formed along an edge of the tooth-cleaning paper, and the dental floss is provided in a single strand or two strands along a margin of the tooth-cleaning paper to be fixed to the tooth-cleaning paper and has an exposed dental floss part formed by each of the plurality of edge cuts of the tooth-cleaning paper. The tooth-cleaning paper of the current invention is advantageous in terms of easily cleaning the teeth and interdental portions of users while not offending other persons at any time and in any place.

2 Claims, 3 Drawing Sheets

TOOTH-CLEANING PAPER COMBINED WITH DENTAL FLOSS

BACKGROUND OF THE INVENTION

1. Field of the Invention

The present invention relates, in general, to a tooth-cleaning paper having dental floss, and more specifically, to a tooth-cleaning paper provided with dental floss, capable of easily cleaning the teeth and interdental portions of users while not giving other persons an unpleasant feeling at desired times and in desired places.

2. Description of the Related Art

Generally, persons brush their teeth after a meal in a predetermined place, such as a washroom, to clean the teeth. However, upon not brushing the teeth, persons swish a mouthful of water in their closed mouths or clean their teeth or interdental portions by use of an unsterilized napkin or a toothpick. Such cleaning actions of the teeth and interdental portions are practically ineffective, and as well, offend other persons.

Therefore, to solve the above problems, there are developed a cleaning paper and dental floss, in which the cleaning paper is used to scrub the teeth so as to hygienically clean the teeth, and the dental floss serves to be inserted between interdental portions so as to clean the interdental portions.

However, since the cleaning paper and the dental floss should be separately purchased, their storage and usage become cumbersome.

In addition, the dental floss is applied in a state of being wound around the fingers of both hands of the user to prevent slipping from the gripping hands.

Hence, the dental floss has difficulties in storage, and practical use thereof causes inconvenience. Also, the portion of the dental floss, which is wound around the fingers of the user, is not further used, thus negating economic benefits.

SUMMARY OF THE INVENTION

Accordingly, it is an object of the present invention to alleviate the problems encountered in the related art and to provide a tooth-cleaning paper combined with dental floss, which is capable of easily cleaning the teeth as well as interdental portions of users while not giving an unpleasant feeling to other persons in desired places, by combining the cleaning paper for use in scrubbing the teeth of the user with the dental floss for use in removal of interdental debris.

In order to accomplish the above object, the present invention provides a tooth-cleaning paper combined with dental floss, wherein the tooth-cleaning paper is formed of a thin paper or a gauze sterilized and wetted with an aqueous fluoride solution and has a plurality of edge cuts formed at edge portions thereof, and the dental floss is provided in a single strand or two strands along a margin of the tooth-cleaning paper to be fixed to the tooth-cleaning paper and has an exposed dental floss part formed by each of the plurality of edge cuts of the tooth-cleaning paper.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Below, a description will be given of a tooth-cleaning paper combined with dental floss, according to an embodiment of the present invention, with reference to the attached drawings.

Figure 1:
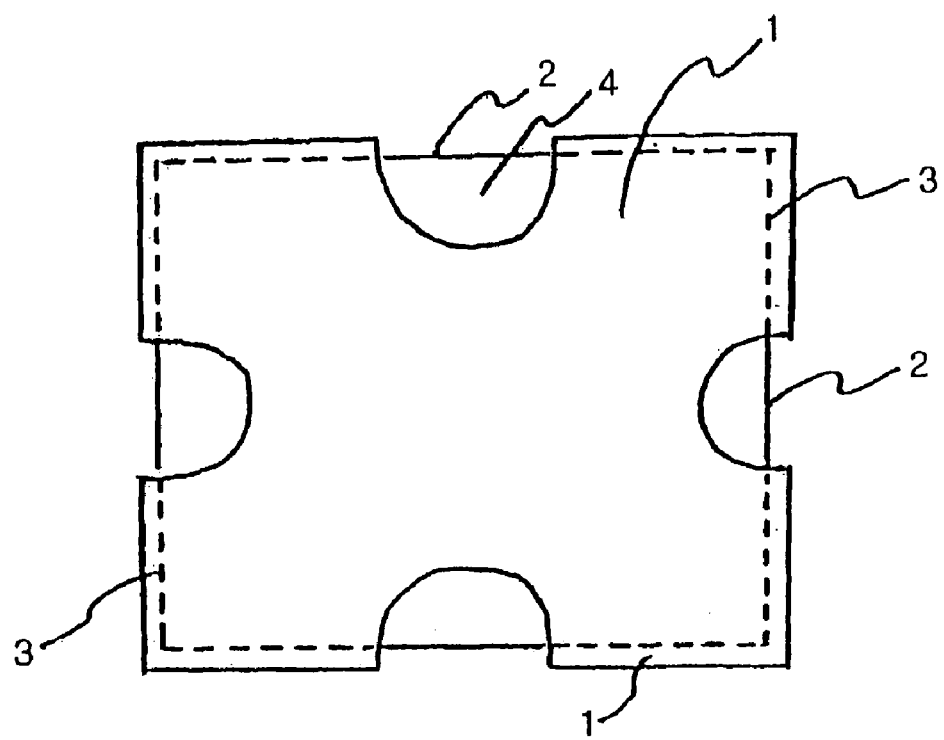
FIG. 1 is a plan view of a tooth-cleaning paper combined with dental floss, according to the present invention.

Referring to FIG. 1, there is shown a plan view of the tooth-cleaning paper combined with dental floss. Additionally, FIG. 2 is a perspective view of the tooth-cleaning paper combined with the dental floss, of which the part A in FIG. 2 is illustrated in FIG. 3.

Figure 2:
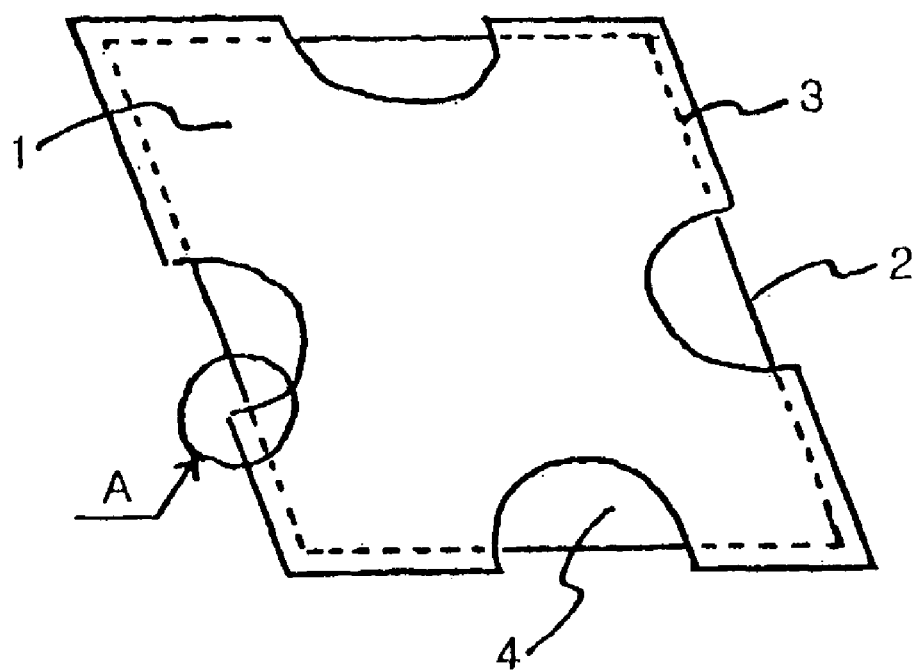
FIG. 2 is a perspective view of the tooth-cleaning paper combined with the dental floss, according to the present invention.
Figure 3:
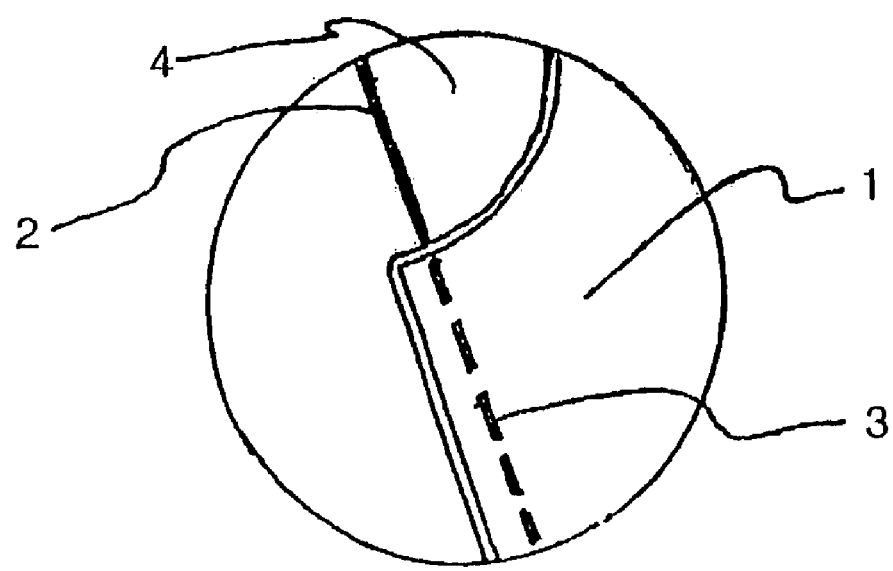
FIG. 3 is an enlarged perspective view of the part A in FIG. 2.

As shown in FIGS. 1 to 3, a tooth-cleaning paper 1 of the present invention includes a plurality of edge cuts 4, and dental floss 3 provided along a margin of the tooth-cleaning paper 1 by means of a fixing process, such as a sewing process or an adhering process, in which the dental floss 3 has exposed dental floss parts 2 formed by each of the plurality of edge cuts 4.

Useful as the tooth-cleaning paper 1, a paper, such as a thin paper or a cosmetic paper, or a textile fabric, such as woven or nonwoven fabrics and gauze, is sterilized and then wetted with distilled water containing fluoride and a perfume safe for humans, to have a suitable moistness.

As such, the tooth-cleaning paper 1 of the present invention has the plurality of edge cuts 4 which are cut out from an edge portion thereof. Although the edge cuts 4 are shown to a semicircular shape, as shown in FIGS. 1 and 2, the edge cuts 4 may be formed into various shapes, such as a polygonal shape.

Further, in the present invention, the dental floss 3 is fixed along the margin of the tooth-cleaning paper 1. At this time, the dental floss 3 is structured to have the exposed dental floss part 2 by being exposed through the edge cuts 4 of the tooth-cleaning paper 1 in the state of being fixed to the tooth-cleaning paper 1.

That is, after the plurality of edge cuts 4 are formed at the edge portions of the tooth-cleaning paper 1, the dental floss 3 is fixed to the margin of the tooth-cleaning paper 1 by means of a sewing process using a backstitch manner or an adhering process using a harmless adhesive. Thereby, the dental floss 3 is externally exposed through the edge cuts 4, to form the exposed dental loss part 2.

As such, it is important that the dental floss 3 is fixed along the margin of the cleaning paper 1 so that the exposed dental floss part 2 of the dental floss 3 is not separated from the tooth-cleaning paper 1 upon cleaning the interdental portions of the user. As the fixing process, a sewing process using a backstitch manner or an adhering process using an adhesive may be adopted.

As for use of the thus structured tooth-cleaning paper of the present invention, an exposed tooth portion of the user is scrubbed with the tooth-cleaning paper 1, and interdental debris is removed by inserting the exposed dental floss part 2 of the dental floss 3 between the interdental portions of the user in the state of the exposed dental floss part 2 in the edge cuts 4 of the tooth-cleaning paper 1 being tight by stretching the tooth-cleaning paper 1 positioned at both sides of the exposed dental floss part 2.

Like this, the tooth-cleaning paper of the present invention is characterized in that the tooth-cleaning paper 1 is integrally formed with the dental floss 3, in which the edge cuts 4 are provided to the tooth-cleaning paper 1 so as to form the exposed dental floss part 2 for easy use of the dental floss 3, thus simply cleaning the interdental portions of the user by means of such an exposed dental floss part 2.

As described above, the present invention provides a tooth-cleaning paper combined with dental floss, which is portably manufactured and is capable of easily cleaning the teeth and interdental portions of users while not offending other persons at any time and in any place.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

The invention claimed is:

1. A tooth-cleaning paper combined with dental floss, wherein the tooth-cleaning paper is formed of a thin paper or a gauze sterilized and wetted with an aqueous fluoride solution and has a plurality of edge cuts formed at edge portions thereof, and the dental floss is provided in a single strand or two strands along a margin of the tooth-cleaning paper to be fixed to the tooth-cleaning paper and has an exposed dental floss part formed by each of the plurality of edge cuts of the tooth-cleaning paper;

wherein the dental floss provided in a single strand or two strands is fixed to the margin of the tooth-cleaning paper by a sewing process.

2. The tooth-cleaning paper according to claim 1, wherein the edge portions of the tooth-cleaning paper are of substantially identical length.

* * * * *